US012618090B2

(12) United States Patent
Zhong et al.

(10) Patent No.: US 12,618,090 B2
(45) Date of Patent: May 5, 2026

(54) METHOD FOR INCREASING THE EXTRACTION RATE OF CHONDROITIN SULFATE PREPARED FROM TILAPIA SKULL

(71) Applicant: GUANGDONG OCEAN UNIVERSITY, Zhanjiang City (CN)

(72) Inventors: Saiyi Zhong, Zhanjiang City (CN); Gege Zuo, Zhanjiang City (CN); Jing Chen, Zhanjiang City (CN); Jianping Chen, Zhanjiang City (CN); Rui Li, Zhanjiang City (CN); Bingbing Song, Zhanjiang City (CN); Kangjian Chen, Zhanjiang City (CN); Xiaofei Liu, Zhanjiang City (CN); Xuejing Jia, Zhanjiang City (CN)

(73) Assignee: GUANGDONG OCEAN UNIVERSITY, Zhanjiang City (CN)

( * ) Notice: Subject to any disclaimer, the term of this patent is extended or adjusted under 35 U.S.C. 154(b) by 539 days.

(21) Appl. No.: 18/015,329

(22) PCT Filed: Mar. 24, 2022

(86) PCT No.: PCT/CN2022/082803
§ 371 (c)(1),
(2) Date: Jan. 10, 2023

(87) PCT Pub. No.: WO2023/082523
PCT Pub. Date: May 19, 2023

(65) Prior Publication Data
US 2024/0247293 A1 Jul. 25, 2024

(30) Foreign Application Priority Data
Nov. 15, 2021 (CN) .......................... 202111344514.5

(51) Int. Cl.
*C12P 19/04* (2006.01)
*C12N 9/54* (2006.01)
*C12N 9/64* (2006.01)
(52) U.S. Cl.
CPC ................ *C12P 19/04* (2013.01); *C12N 9/54* (2013.01); *C12N 9/6408* (2013.01); *C12Y 304/21062* (2013.01)

(58) Field of Classification Search
CPC ......... C12P 19/04; C12N 9/54; C12N 9/6408; C12Y 304/21062; C08B 37/0003; C08B 37/0069
See application file for complete search history.

(56) References Cited

FOREIGN PATENT DOCUMENTS

| CN | 1544645 | A | 11/2004 | |
| CN | 101012288 | A | 8/2007 | |
| CN | 101348815 | A | 1/2009 | |
| CN | 101348815 | * | 10/2009 | ............. C12P 19/04 |
| CN | 105884931 | A | 8/2016 | |
| CN | 113773414 | A | 12/2021 | |

OTHER PUBLICATIONS

Oliveira 1 et al., Characteristics of Chondroitin Sulfate Extracted of Tilapia (*Oreochromis niloticus*) Processing. Procedia Engineering, 2017, vol. 200: 193-199 (Year: 2017).*
Zuo et al., Preparation, Physicochemical Properties and Structural Characterization of Chondroitin Sulfate from Tilapia Processing By-Products. Food Science, 2022, vol. 43, No. 24, pp. 67-73 (English Translation). (Year: 2022).*

* cited by examiner

*Primary Examiner* — Ganapathirama Raghu
(74) *Attorney, Agent, or Firm* — Hemisphere Law, PLLC

(57) ABSTRACT

This present disclosure provides a method for preparing chondroitin sulfate from tilapia skull, including enzymatic hydrolyzing tilapia skull powder by Savinase 16L to obtain Savinase 16L enzymatic hydrolysate, re-enzymatic hydro-lyzing the Savinase 16L enzymatic hydrolysate by 2709 alkaline protease, then separating and purificating the solution by ethanol and cetylpyridine chloride to obtain the chondroitin sulfate. The present disclosure adopts a compound enzymatic hydrolyzing method by Savinase 16L and 2709 alkaline protease to effectively achieve the efficient extraction of chondroitin sulfate of tilapia skull powder, and further achieve the purification of chondroitin sulfate by ethanol and cetylpyridine chloride, so that tilapia by-products can be utilized with high value.

3 Claims, No Drawings

METHOD FOR INCREASING THE EXTRACTION RATE OF CHONDROITIN SULFATE PREPARED FROM TILAPIA SKULL

TECHNICAL FIELD

The present disclosure belongs to the field of bioengineering technology and relates to a method for improving the extraction rate of chondroitin sulfate prepared from tilapia skull.

BACKGROUND

Chondroitin Sulfate (CS) is a highly sulfated glycosaminoglycan consisting of alternating D-glucuronic acid and N-acetyl-d-galactosamine linked disaccharide unit. Chondroitin sulfate has many isomers according to the number and types of sulfate groups linked at different positions of glucuronic acid (GlcA) and N-acetylgalactosamine (GalNAc). Based on existing research, chondroitin sulfate has a variety of biological activities such as anti-inflammatory, antioxidant, anticoagulation, lipid-lowering and anti-tumor, and can effectively inhibit thrombosis, hinder the formation of atherosclerotic plaque and reduce the lipid index by regulating growth factors, thus can prevent cardiovascular diseases. In addition, chondroitin sulfate can also be used as a food additive, a health food and a dietary supplement.

Commercial chondroitin sulfate was mainly extracted from bovine cartilage, pig cartilage, shark cartilage, but due to the mad cow disease, the foot-and-mouth disease and other diseases, the development of terrestrial sources of chondroitin sulfate was limited. In recent years, for shark resources have become increasingly scarce and are expensive, so it is urgent to find a new source of chondroitin sulfate to replace shark raw materials. Tilapia is a tropical teleost fish characterized as fast growth, high yield, strong fecundity, etc. The total production of freshwater tilapia in China is increasing, and the processing by-products of tilapia are also increasing, such as fish skull, fish tail, fish bone, fish scale, fish skin and internal organs, etc., which are usually discarded or indiscriminately processed into low-value products such as feed, making a large number of resources have not been fully developed and utilized.

The extraction of chondroitin sulfate from tilapia skull is one of the effective measures to transform low-value tilapia processing by-products to high-value products. However, it should be pointed out that chondroitin sulfate is not only easy to degrade under the condition of high temperature and strong acid, so that its molecular weight is reduced, but also can be degraded under the action of chondroitin sulfate lyase. Traditional extraction methods of chondroitin sulfate include alkali extraction method, salt extraction method, alkali salt method, ultrasonic assistance method, etc. Among them, the alkali salt method will pollute the environment and will also make chondroitin sulfate degradation, the ultrasonic assistance method have a high demand for time and may produce impurities, and the extraction efficiency of chondroitin sulfate by the neutral salt method is low. Separation and purification methods of chondroitin sulfate include chromatography method, electrophoretic ultrafiltration method, anion exchange resin method, etc. However, these methods have the problems of complex steps, long production cycle and high cost.

SUMMARY

The purpose of the present disclosure is to provide an efficient method for preparing chondroitin sulfate from fish skull.

For the above purposes, this application resolves this requirement in the field by providing a method for increasing the extraction rate of chondroitin sulfate prepared from tilapia skull.

On the one hand, the present disclosure relates to a method for increasing the extraction rate of chondroitin sulfate prepared from tilapia skull including: enzymatic hydrolyzing tilapia skull powder by subtilisin protease (sold under the trademark SAVINASE 16L) to form a first enzymatic hydrolysate; re-enzymatic hydrolyzing the first enzymatic hydrolysate by an alkaline protease (sold under the trademark 2709 ALKALINE PROTEASE) to form a second enzymatic hydrolysate; then separating and purificating the second enzymatic hydrolysate by ethanol and cetylpyridine chloride to obtain the chondroitin sulfate; wherein a mass-volume ratio of the tilapia skull powder to the subtilisin protease (sold under the trademark SAVINASE 16L) is 1:15 to 1:25 in g:μL; a mass-volume ratio of the alkaline protease (sold under the trademark 2709 ALKALINE PROTEASE) to the first enzymatic hydrolysate is 5:1 to 6:1 in mg:mL.

Further, in the method of improving the extraction rate of chondroitin sulfate prepared from tilapia skull provided by the present disclosure, the enzymatic hydrolyzing tilapia skull powder by the subtilisin protease (sold under the trademark SAVINASE 16L) to form the first enzymatic hydrolysate includes: adding the tilapia skull powder into $Na_2CO_3$ solution; enzymatic hydrolyzing the mixed solution; inactivating enzymes to obtained solution to form the first enzymatic hydrolysate.

Further, in the method of improving the extraction rate of chondroitin sulfate prepared from tilapia skull provided by the present disclosure, the re-enzymatic hydrolyzing the first enzymatic hydrolysate by an alkaline protease (sold under the trademark 2709 ALKALINE PROTEASE) to form the second enzymatic hydrolysate includes: adding the alkaline protease into the first enzymatic hydrolysate which has been inactivated enzymes, enzymatic hydrolyzing mixed solution at 50° C. for 2 hours; inactivating enzymes to obtained solution; cooling and centrifugating the solution; collecting a first supernatant to obtain the second enzymatic hydrolysate.

Further, in the method of improving the extraction rate of chondroitin sulfate prepared from tilapia skull by the present disclosure, after the re-enzymatic hydrolyzing the first enzymatic hydrolysate, and before the separating and purificating the second enzymatic hydrolysate by ethanol and cetylpyridine chloride to obtain the chondroitin sulfate, further comprises: adding trichloroacetic acid into the second enzymatic hydrolysate; collecting a second supernatant by centrifugation.

Specifically, the present disclosure provides a method for improving the extraction rate of chondroitin sulfate prepared from tilapia skull, including: adding the tilapia skull powder into 50 mM $Na_2CO_3$ solution, adjusting pH of the solution to neutral, and enzymatic hydrolyzing the solution at 55° C. for 4 hours; then adding the Savinase16L into the solution and stirring the solution in a water bath at 55° C. for 4 h; inactivating enzymes to the solution to obtain a first enzymatic hydrolysate; adding an alkaline protease (sold under the trademark 2709 ALKALINE PROTEASE) into the first enzymatic hydrolysate, re-enzymatic hydrolyzing the enzymatic hydrolysate at 50° C. for 2 hours, and then inactivating enzymes to the solution to obtain a second enzymatic hydrolysate; adding trichloroacetic acid into the second enzymatic hydrolysate, stirring and then standing the second enzymatic hydrolysate for 3 h, obtaining supernatant by centrifugation; adding absolute ethyl alcohol into the supernatant and processing alcohol precipitation at 4° C., then collecting a first precipitate by centrifugation; dissolving the first precipitate into 20 mM $Na_2SO_4$ solution, subsequently, slowly adding cetylpyridium chloride solution into the solution, then collecting a second precipitate by centrifugation; dissolving the second precipitate into NaCl-ethanol aqueous solution, adding ethyl alcohol and then standing the solution at 4° C., collecting a third precipitate by centrifugation; dissolving the third precipitate into water for clarification, and then freeze-drying the precipitate to obtain the chondroitin sulfate.

Further, in the method of improving the extraction rate of chondroitin sulfate prepared from tilapia skull provided by the present disclosure, the condition of inactivating enzymes to obtain the first enzymatic hydrolysate and the condition of inactivating enzymes to obtain the second enzymatic hydrolysate are all 100° C. for 10 min and the hydrolysate which has been inactivated enzymes are all cooled by ice-water bath; the condition of centrifugation in each step are 8000 r/min for 20 min at 4° C.

Further, in the method for improving the extraction rate of chondroitin sulfate prepared from tilapia skull provided by the present disclosure, the mass concentration of the cetylpyridium chloride solution is 6%.

Further, in the method for improving the extraction rate of chondroitin sulfate prepared from tilapia skull provided by the present disclosure, the NaCl-ethanol aqueous solution is a mixture of 2M NaCl solution and ethyl alcohol, and the volume ratio of the 2M NaCl solution to the ethyl alcohol is 100:15.

On the other hand, the present disclosure provides the prepared method of the tilapia skull powder comprises: boiling tilapia skulls in 80° C. to 100° C. water to remove excess muscles and other impurities, soaking the tilapia skulls in ethanol, and drying and crushing the tilapia skulls into powder to obtain the tilapia skull powder.

On the other hand, the present disclosure discloses the use of subtilisin protease (sold under the trademark SAVINASE 16L) in the extraction of chondroitin sulfate.

Further, in the method of improving the extraction rate of chondroitin sulfate prepared from tilapia skull provided by the present disclosure, the enzymatic hydrolyzing tilapia skull powder by the subtilisin protease (sold under the trademark SAVINASE 16L) to form the first enzymatic hydrolysate further includes: after adding the tilapia skull powder into $Na_2CO_3$ solution, adjusting pH of mixed solution to neutral.

Further, in the method of improving the extraction rate of chondroitin sulfate prepared from tilapia skull provided by the present disclosure, condition of the enzymatic hydrolyzing the mixed solution is at 55° C. for 4 hours; condition of the inactivating enzymes to the obtained solution is at 100° C. for 10 min; after the inactivating enzymes to the obtained solution, cooling the solution which has been inactivated enzymes to room temperature to form the first enzymatic hydrolysate.

Further, in the method of improving the extraction rate of chondroitin sulfate prepared from tilapia skull provided by the present disclosure, the concentration of the $Na_2CO_3$ solution is 50 mM, and the mass-volume ratio of the tilapia skull powder to the 50 mM $Na_2CO_3$ solution is 1:25.

Further, in the method of improving the extraction rate of chondroitin sulfate prepared from tilapia skull provided by the present disclosure, condition of inactivating enzymes to obtained solution is at 100° C. for 10 min; the solution is cooled to 4° C.; the first supernatant is collected by centrifugation.

Further, in the method of improving the extraction rate of chondroitin sulfate prepared from tilapia skull provided by the present disclosure, the trichloroacetic acid is weighed equal to 3% to 5% of the weight of the second enzymatic hydrolysate.

Further, in the method of improving the extraction rate of chondroitin sulfate prepared from tilapia skull provided by the present disclosure, the separating and purificating the second enzymatic hydrolysate by ethanol and cetylpyridine chloride to obtain the chondroitin sulfate comprises: adding absolute ethyl alcohol into the second supernatant and alcohol precipitating at 4° C., then collecting a first precipitate by centrifugation; dissolving the first precipitate into $Na_2SO_4$ solution; slowly adding cetylpyridium chloride solution into the $Na_2SO_4$ solution; collecting a second precipitate by centrifugation; dissolving the second precipitate into NaCl-ethanol aqueous solution; adding ethyl alcohol and collecting a third precipitate by centrifugation; dissolving the third precipitate into water for clarification, and then freeze-drying the precipitate to obtain chondroitin sulfate.

Further, in the method of improving the extraction rate of chondroitin sulfate prepared from tilapia skull provided by the present disclosure, the volume ratio of absolute ethanol and the supernatant is 3:1; wherein the volume ratio of absolute ethanol and the NaCl-ethanol aqueous solution is 3:1.

Further, in the method of improving the extraction rate of chondroitin sulfate prepared from tilapia skull provided by the present disclosure, the mass concentration of the cetylpyridium chloride solution is 6%.

Further, in the method of improving the extraction rate of chondroitin sulfate prepared from tilapia skull provided by the present disclosure, the NaCl-ethanol aqueous solution is a mixture of 2M NaCl solution and ethyl alcohol, and the volume ratio of the 2M NaCl solution to the ethyl alcohol is 100:15.

Further, in the method of improving the extraction rate of chondroitin sulfate prepared from tilapia skull provided by the present disclosure, the mass-volume ratio of the tilapia skull powder to the 50 mM $Na_2CO_3$ solution is 1:25; wherein the volume ratio of absolute ethanol and the supernatant is 3:1; wherein the volume ratio of absolute ethanol and the NaCl-ethanol aqueous solution is 3:1.

Compared with the prior art, the present disclosure has the following beneficial effects or advantages:

(1) The present disclosure provides a method for improving the extraction rate of chondroitin sulfate prepared from tilapia skull. The method has mild reaction conditions and can maximize the degree of chondroitin sulfate without degradation in the extraction process;

(2) The present disclosure provides a method for improving the extraction rate of chondroitin sulfate prepared from tilapia skull, and the method adopts compound enzymes to achieve the efficient extraction of chondroitin sulfate from tilapia skull;

(3) The present disclosure provides a method for improving the extraction rate of chondroitin sulfate prepared from tilapia skull, and the method effectively realizes the purification of chondroitin sulfate by taking ethyl alcohol precipitation and adopting cetylpyridine chloride.

DETAILED DESCRIPTION

In the following, the technical solution of the present disclosure is described in conjunction with embodiments, but the present disclosure is not limited to the following embodiments.

Example 1

This embodiment provides an experiment for preparation of chondroitin sulfate by a method for increasing the extraction rate of chondroitin sulfate from tilapia skull.

(1) Tilapia skulls were boiled at 100° C. for 30 min to remove excess muscles and other impurities, and then were soaked in ethanol overnight. After that, wet skulls were put into 65° C. oven to dry for 8 h, and then were crushed into powder. Obtained tilapia skull powder was stored at −80° C. for future use.

(2) 10 g of the tilapia skull powder prepared in (1) was got. 50 mM (m mol/L) $Na_2CO_3$ solution was mixed with the tilapia skull powder according to a mass-volume ratio of 1:25 (m/v), and pH of mixed solution was then adjusted to 7.0. After that, 200 μL of Savinase16L was added into the mixed solution, the mixed solution containing Savinase16L was then stirred in a water bath at 55° C. for 4 h, and then the solution was inactivated enzymes at 100° C. for 10 min. Subsequently, obtained solution was cooled to room temperature to form a first enzymatic hydrolysate (first enzymatic hydrolysate).

(3) an alkaline protease (sold under the trademark 2709 ALKALINE PROTEASE) was added into the first enzymatic hydrolysate obtained in (2) according to a mass-volume ratio of 5.4 mg/ml, and that is the mass-volume ratio of the alkaline protease to the first enzymatic hydrolysate is 5.4:1 in mg:mL. Mixed solution was reacted in a water bath at 50° C. for 2 h, reacted solution was then inactivated enzymes at 100° C. for 10 min. Subsequently, the reacted solution was cooled to 4° C. and was centrifugated at 8000 r/min for 20 min; a first supernatant was collected to obtain a second enzymatic hydrolysate.

(4) Trichloroacetic acid weighed equal to 5% of the weight of the first supernatant collected in (3) was added into the second enzymatic hydrolysate and stood for 3 h, a second supernatant was collected by centrifugation (the centrifugation conditions were the same as in step (3)), and then was alcohol precipitated by 3 times absolute ethyl alcohol at 4° C. overnight. 3 times absolute ethyl alcohol means a volume of the absolute ethyl alcohol is 3 times of the volume of the second supernatant. A first precipitate was collected by centrifugation (same centrifugation conditions as in step (3)).

(5) The first precipitate obtained in (4) was dissolved in 20 mM $Na_2SO_4$ solution, subsequently, cetylpyridium chloride solution with a mass concentration of 6% was slowly added into the $Na_2SO_4$ solution until there is no new precipitate, then a second precipitate was collected by centrifugation (same centrifugation conditions as in step (3)).

(6) The second precipitate obtained in (5) was dissolved in 2M NaCl-ethanol (100:15) aqueous solution, and then was alcohol precipitated by 3 times absolute ethyl alcohol at 4° C. overnight. The NaCl-ethanol aqueous solution is a mixture of 2M NaCl solution and absolute ethyl alcohol, and the volume ratio of the 2M NaCl solution and absolute ethyl alcohol is 100:15. A third precipitate was obtained by centrifugation, and then was dissolved in distilled water for 24 h for clarification, then be concentrated and freeze-dried to obtain chondroitin sulfate.

Example 2

This embodiment provides an experiment for the preparation of chondroitin sulfate by a method for increasing the extraction rate of chondroitin sulfate from tilapia skull.

The operation process was similar to example 1. The difference was that in step (2), the mass-volume ratio of the tilapia skull powder to the subtilisin protease (sold under the trademark SAVINASE 16L) was 1:15 in g: μL, and in step (3), the mass-volume ratio of the alkaline protease to the first enzymatic hydrolysate was 5:1 in mg:mL.

Example 3

This embodiment provides an experiment for the preparation of chondroitin sulfate by a method for increasing the extraction rate of chondroitin sulfate from tilapia skull.

The operation process was similar to example 1. The difference was that in step (2), the mass-volume ratio of the tilapia skull powder to the subtilisin protease (sold under the trademark SAVINASE 16L) was 1:25 in g:μL and in step (3), the mass-volume ratio of the alkaline protease to the first enzymatic hydrolysate was 6:1 in mg:mL.

Example 4

This embodiment provides an experiment for the preparation of chondroitin sulfate by a method for increasing the extraction rate of chondroitin sulfate from tilapia skull.

The operation process was similar to example 1. The difference was that in step (4), the additional weight of trichloroacetic acid is 4% of the weight of the first supernatant.

Example 5

This embodiment provides an experiment for the preparation of chondroitin sulfate by a method for increasing the extraction rate of chondroitin sulfate from tilapia skull.

The operation process was similar to example 1. The difference was that in step (4), the additional weight of trichloroacetic acid is 3% of the weight of the first supernatant.

Example 6

This embodiment provides an experiment for the preparation of chondroitin sulfate by a method for increasing the extraction rate of chondroitin sulfate from tilapia skull.

This embodiment provides the purity and extraction rate of the chondroitin sulfate prepared in Examples 1 to 5.

The purity of the chondroitin sulfate was determined by a sulfuric acid-carbazole method, and the content of the chondroitin sulfate was determined by using pure chondroitin sulfate as standard, and the extraction rate of the chondroitin sulfate in different examples was calculated. The purity and extraction rate of the chondroitin sulfate prepared in examples 1-5 are shown in Table 1.

Table 1, purity and extraction rate of the chondroitin sulfate prepared in Examples 1-5

| | purity % | extraction rate % |
|---|---|---|
| Example 1 | 90.37 | 1.02 |
| Example 2 | 90.29 | 1.02 |
| Example 3 | 90.30 | 1.02 |
| Example 4 | 89.42 | 0.91 |
| Example 5 | 90.12 | 1.00 |

The results in Table 1 show that in the method of increasing the extraction rate of chondroitin sulfate prepared from tilapia skull provided by the present disclosure, when the mass-volume ratio of the tilapia skull powder and the subtilisin protease (sold under the trademark SAVINASE 16L) is 1:15 to 1:25 in g:μL, the mass-volume ratio of the alkaline protease to the first enzymatic hydrolysate is 5:1 to 6:1 in mg:mL, and the additional weight of trichloroacetic acid is 3% to 4% of the weight of the first supernatant, chondroitin sulfate can be effectively prepared. When the mass-volume ratio of the tilapia skull powder and the subtilisin protease (sold under the trademark SAVINASE 16L) was 1:20 in g:μL, the mass-volume ratio of the alkaline protease to the first enzymatic hydrolysate was 5.4:1 in mg:mL, and the additional weight of trichloroacetic acid was 5% of the weight of the first supernatant, the purity and extraction rate of chondroitin sulfate were the highest.

Example 7

This embodiment provides experiments of the effect of enzymatic hydrolysis by different proteases on the purity and extraction rate of chondroitin sulfate.

In experiment 1, tilapia skulls were boiled at 100° C. for 30 min to remove excess muscle and other impurities, and then were soaked in ethanol overnight. After that, wet skulls were put into 65° C. oven for 8 h, and then were crushed into powder. Obtained tilapia skull powder was stored at −80° C. for future use. 10 g of the tilapia skull powder prepared in (1) was got. 50 mM $Na_2CO_3$ solution was mixed with the tilapia skull powder according to a mass-volume ratio of 1:25 (m/v), and pH of mixed solution was then adjusted to 7.0. After that, 200 μL of subtilisin protease (sold under the trademark SAVINASE 16L) was added into the mixed solution, and the mixed solution containing subtilisin protease (sold under the trademark SAVINASE 16L) was stirred in a water bath at 55° C. for 6 h, and then the solution was inactivated enzymes at 100° C. for 10 min. Subsequently, obtained solution was cooled to room temperature to form enzymatic hydrolysate. Trichloroacetic acid weighed equal to 5% of the weight of the enzymatic hydrolysate was added into the enzymatic hydrolysate and stood for 3 h. Supernatant was collected by centrifugation, and then was alcohol precipitated by 3 times ethyl alcohol at 4° C. overnight. A first precipitate was collected by centrifugation. The first precipitate was dissolved in 20 mM $Na_2SO_4$ solution. Subsequently, cetylpyridium chloride solution with a mass concentration of 6% was slowly added until there is no new precipitate, then a second precipitate was collected by centrifugation. The second precipitate was re-dissolved in 2M NaCl-ethanol (100:15) aqueous solution, and then was alcohol precipitated by 3 times ethyl alcohol at 4° C. overnight. A third precipitate was obtained by centrifugation, and then was dissolved in distilled water for 24 h for clarification, then be concentrated and freeze-dried to obtain chondroitin sulfate. Experiment 2 was similar to experiment 1, the difference was that: in experiment 2, 1.35 g of an alkaline protease (sold under the trademark 2709 ALKA-LINE PROTEASE) was added to replace the subtilisin protease (sold under the trademark SAVINASE 16L) added in experiment 1 and the enzymatic hydrolyzing time was 20 h. Experiment 3 was similar to experiment 1, the difference was that: in experiment 3, 1.35 g of trypsin was added to replace the subtilisin protease (sold under the trademark SAVINASE 16L) added in experiment 1 and the enzymatic hydrolyzing time was 24 h. Experiment 4 was similar to experiment 1, the difference was that: in experiment 4, 1.35 g of papain was added to replace the subtilisin protease (sold under the trademark SAVINASE 16L) added in experiment 1 and the enzymatic hydrolyzing time was 8 h. Experiment 5 was similar to experiment 1, the difference was that: in experiment 5, 1.35 g of neutral protease was added to replace the subtilisin protease (sold under the trademark SAVINASE 16L) added in experiment 1 and the enzymatic hydrolyzing time was 16 h. Experiment 6 was similar to experiment 1, the difference was that: in experiment 6, 1.35 g of pepsin was added to replace the subtilisin protease (sold under the trademark SAVINASE 16L) added in experiment 1 and the enzymatic hydrolyzing time was 24 h. Experiment 7 was similar to experiment 1, the difference was that: in experiment 7, 1.35 g of protamex protease was added to replace the subtilisin protease (sold under the trademark SAVINASE 16L) added in experiment 1 and the enzymatic hydrolyzing time was 20 h. The purity of the chondroitin sulfate was determined by a sulfuric acid-carbazole method, and the content of the chondroitin sulfate was determined by using pure chondroitin sulfate as standard, and the extraction rate of the chondroitin sulfate in different methods was calculated. The results of the experiments are shown in Table 2.

Table 2, purity and extraction rate of the chondroitin sulfate prepared by different proteinase

| Method(proteinase) | extraction rate % | purity % |
|---|---|---|
| Savinase 16L | 0.81 | 90.01 |
| 2709 alkaline protease | 0.64 | 89.01 |
| trypsin | 0.37 | 88.21 |
| papain | 0.57 | 89.75 |
| neutral protease | 0.53 | 90.12 |
| pepsin | 0.43 | 89.91 |
| Protamex protease | 0.72 | 89.56 |

It can be seen that in Table 2, it is found in the present disclosure that comparing with other enzymatic hydrolyzing methods, the enzymatic hydrolyzing method combining subtilisin protease (sold under the trademark SAVINASE 16L) and an alkaline protease (sold under the trademark 2709 ALKALINE PROTEASE) significantly improves the extraction rate and purity of chondroitin sulfate prepared from tilapia skull. Possibly because of subtilisin protease (sold under the trademark SAVINASE 16L) can release chondroitin sulfate better, thus the extraction effect is better.

Example 8

This embodiment provides experiments of the effect of subtilisin protease (sold under the trademark SAVINASE 16L) with different enzymatic hydrolyzing time, different additional amount, and different enzymatic hydrolyzing pH on the purity and extraction rate of chondroitin sulfate.

Experiment 8 was similar to example 1, the difference was that in experiment 8 the enzymatic hydrolyzing time of subtilisin protease (sold under the trademark SAVINASE 16L) was 6 h. Experiment 9 was similar to example 1, the difference was that in experiment 9 the enzymatic hydrolyzing time of subtilisin protease (sold under the trademark SAVINASE 16L) was 10 h. Experiment 10 was similar to example 1, the difference was that in experiment 10 the enzymatic hydrolyzing pH of subtilisin protease (sold under the trademark SAVINASE 16L) was 7.5. The purity of the chondroitin sulfate was determined by a sulfuric acid-carbazole method, and the content of the chondroitin sulfate was determined by using pure chondroitin sulfate as standard, and the extraction rate of the chondroitin sulfate in different methods was calculated. The results of the experiments are shown in Table 3.

Table 3, purity and extraction rate of the chondroitin sulfate prepared in different enzymatic hydrolyzing conditions

|  | extraction rate % | purity % |
| --- | --- | --- |
| Experiment 8 | 0.93 | 90.13 |
| Experiment 9 | 0.75 | 89.94 |
| Experiment 10 | 0.89 | 90.05 |
| Example 1 | 1.02 | 90.37 |

The results in Table 3 show that: the method of increasing the extraction rate of chondroitin sulfate, prepared from tilapia skull, provided by the present disclosure, can significantly improves the extraction rate and purity of chondroitin sulfate. When the additional amount of the subtilisin protease (sold under the trademark SAVINASE 16L) compared to the weight of the tilapia skull powder was 20 μL:1 g, the enzymatic hydrolyzing time was 4 h, and the enzymatic hydrolyzing pH was 7, the purity and extraction rate of chondroitin sulfate prepared from tilapia skull were the highest.

As mentioned above, the implementation of the above examples can better realize the present disclosure and describes only the selection method of the present disclosure, and is not to limit the scope of the present disclosure. Under the premise of not out of the present disclosure design spirit, various changes and improvements of the present disclosure made by those of ordinary skill in the art, all should fall into the certain protection scope of the present disclosure.

What is claimed is:

1. A method for increasing the extraction rate of chondroitin sulfate prepared from tilapia skull comprising:

enzymatic hydrolyzing tilapia skull powder by subtilisin protease (SAVINASE 16L) to form a first enzymatic hydrolysate; re-enzymatic hydrolyzing the first enzymatic hydrolysate by an alkaline protease (2709 ALKALINE PROTEASE) to form a second enzymatic hydrolysate; then separating and purificating the second enzymatic hydrolysate by ethanol and cetylpyridine chloride to obtain the chondroitin sulfate; wherein a mass-volume ratio of the tilapia skull powder to the subtilisin protease (SAVINASE 16L) is 1:15 to 1:25 in g:μL;

a mass-volume ratio of the alkaline protease (2709 ALKALINE PROTEASE) to the subtilisin protease (SAVINASE 16L) enzymatic hydrolysate is 5:1 to 6:1 in mg:mL; and wherein the method comprises:

adding the tilapia skull powder into 50 mM $Na_2CO_3$ solution, adjusting pH of the mixed solution to neutral, and enzymatic hydrolyzing the mixed solution at 55° C. for 4 hours; then adding the subtilisin protease (SAVINASE 16L) into the mixed solution and stirring the mixed solution in a water bath at 55° C. for 4 h; inactivating enzymes to the mixed solution to obtain a first enzymatic hydrolysate;

adding alkaline protease into the first enzymatic hydrolysate, enzymatic hydrolyzing the first enzymatic hydrolysate at 50° C. for 2 hours, and then inactivating enzymes to reacted solution to obtain a second enzymatic hydrolysate;

adding trichloroacetic acid into the second enzymatic hydrolysate, stirring and then standing the second enzymatic hydrolysate for 3 h, obtaining supernatant by centrifugation;

adding absolute ethyl alcohol into the supernatant and alcohol precipitating at 4° C.', then collecting a first precipitate by centrifugation;

dissolving the first precipitate into 20 mM $Na_2SO_4$ solution, subsequently, slowly adding cetylpyridium chloride solution into the $Na_2SO_4$ solution, then collecting a second precipitate by centrifugation;

dissolving the second precipitate into NaCl-ethanol aqueous solution, adding ethyl alcohol and then standing the solution at 4° C., collecting a third precipitate by centrifugation;

dissolving the third precipitate into water for clarification, and then freeze-drying the precipitate to obtain chondroitin sulfate; and wherein the NaCl-ethanol aqueous solution is a mixture of 2M NaCl solution and ethyl alcohol, and the volume ratio of the 2M NaCl solution to the ethyl alcohol is 100:15.

2. The method of claim 1, wherein the condition of inactivating enzymes to obtain the first enzymatic hydrolysate and the condition of inactivating enzymes to obtain the second enzymatic hydrolysate are all 100° C. for 10 min and solution are all cooled by ice-water bath; the condition of centrifugation in each step are all 8000 r/min for 20 min at 4° C.

3. The method of claim 1, wherein the mass concentration of the cetylpyridium chloride solution is 6%.

* * * * *